(12) United States Patent
Gewehr et al.

(10) Patent No.: US 7,799,334 B2
(45) Date of Patent: Sep. 21, 2010

(54) PYRAZOLECARBOXAMIDES

(75) Inventors: Markus Gewehr, Kastellaun (DE); Jochen Dietz, Mannheim (DE); Thomas Grote, Wachenheim (DE); Wassilios Grammenos, Ludwigshafen (DE); Udo Hünger, Mannheim (DE); Bernd Müller, Frankenthal (DE); Frank Schieweck, Heβheim (DE); Anja Schwögler, Mannheim (DE); Jan Klaas Lohmann, Mannheim (DE); Joachim Rheinheimer, Ludwigshafen (DE); Jens Renner, Mannheim (DE); Peter Schäfer, Ottersheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 512 days.

(21) Appl. No.: 11/919,588

(22) PCT Filed: May 10, 2006

(86) PCT No.: PCT/EP2006/062219

§ 371 (c)(1),
(2), (4) Date: Oct. 30, 2007

(87) PCT Pub. No.: WO2006/120219

PCT Pub. Date: Nov. 16, 2006

(65) Prior Publication Data

US 2009/0036305 A1 Feb. 5, 2009

(30) Foreign Application Priority Data

May 11, 2005 (DE) .................. 10 2005 022 651

(51) Int. Cl.
| A61K 31/16 | (2006.01) |
| A01N 25/00 | (2006.01) |
| C07D 231/00 | (2006.01) |
| A01N 25/26 | (2006.01) |
| A01N 37/18 | (2006.01) |

(52) U.S. Cl. .................. 424/405; 504/100; 514/599; 514/613; 514/614; 514/628; 548/374.1

(58) Field of Classification Search .................. None
See application file for complete search history.

(56) References Cited

U.S. PATENT DOCUMENTS 5,330,995 A 7/1994 Eicken et al.
5,438,070 A 8/1995 Eicken et al.
5,480,897 A 1/1996 Eicken et al.
5,556,988 A 9/1996 Eicken et al.
5,589,493 A 12/1996 Eicken et al.
6,147,104 A 11/2000 Eicken et al.
6,369,093 B1 4/2002 Elbe et al.
2006/0116414 A1 6/2006 Dunkel et al.

FOREIGN PATENT DOCUMENTS

| DE | 10200502265.5 | * 5/2006 |
| EP | 0 545 099 A2 | 6/1993 |
| EP | 0 589 301 A1 | 3/1994 |
| JP | 8-176112 A | 7/1996 |
| JP | 9-132567 A | 5/1997 |
| WO | WO-99/09013 A1 | 2/1999 |
| WO | WO-00/14071 A2 | 3/2000 |
| WO | WO-01/42223 A1 | 6/2001 |
| WO | WO-03/070705 A1 | 8/2003 |

* cited by examiner

*Primary Examiner*—Ernst V Arnold
(74) *Attorney, Agent, or Firm*—Birch, Stewart, Kolasch & Birch, LLP

(57) ABSTRACT

The present invention relates to pyrazolecarboxamides of the formula I

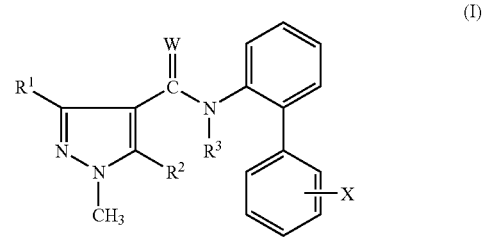

(I)

in which the variables are as defined below:
X is trifluoromethyl;
$R^1$ is F, Cl, Br, $C_1$-$C_4$-alkyl or $C_1$-$C_4$-haloalkyl;
$R^2$ is hydrogen, halogen or $C_1$-$C_4$-alkyl;
$R^3$ is hydrogen, $C_1$-$C_4$-alkyl, $C_1$-$C_4$-haloalkyl, $C_2$-$C_4$-alkenyl, $C_2$-$C_4$-alkynyl or $C_3$-$C_6$-cycloalkyl;
W is O or S;
with the proviso that, if $R^3$ is hydrogen and W is oxygen,
a) $R^1$ and $R^2$ are not simultaneously methyl and F, respectively;
b) $R^1$ and $R^2$ are not simultaneously trifluoromethyl and hydrogen or fluorine, respectively.
to processes for preparing these compounds, to seeds and compositions comprising them and to methods for controlling harmful fungi.

11 Claims, No Drawings

PYRAZOLECARBOXAMIDES

This application is a 371 of PCT/EP2006/062219 filed on May 10, 2006 and claims foreign priority to German 102005022651.5 filed on May 11, 2005.

The present invention relates to pyrazolecarboxamides of the formula I

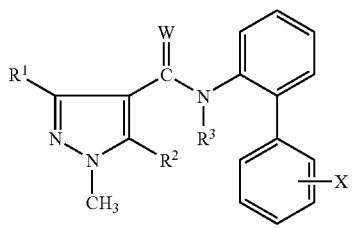

(I)

in which the variables are as defined below:
X is trifluoromethyl;
$R^1$ is F, Cl, bromine, $C_1$-$C_4$-alkyl or $C_1$-$C_4$-haloalkyl;
$R^2$ is hydrogen, halogen or $C_1$-$C_4$-alkyl;
$R^3$ is hydrogen, $C_1$-$C_4$-alkyl, $C_1$-$C_4$-haloalkyl, $C_2$-$C_4$-alkenyl, $C_2$-$C_4$-alkynyl or $C_3$-$C_6$-cycloalkyl;
W is oxygen or sulfur.

with the proviso that, if $R^3$ is hydrogen and W is oxygen,
a) $R^1$ and $R^2$ are not simultaneously methyl and fluorine, respectively;
b) $R^1$ and $R^2$ are not simultaneously trifluoromethyl and hydrogen or fluorine, respectively.

Moreover, the invention relates to processes for preparing these compounds, to compositions comprising them and to methods for their use for controlling harmful fungi.

Pyrazolecarboxamides having fungicidal action are known from the literature. Thus, for example, EP-A 545 099 and EP-A 589 301 describe amides of the type of compounds I which are monosubstituted at the biphenyl group.

The general formula of the biocides described in JP-A 08/176,112 also includes pyrazolecarboxamides having a monosubstituted biphenyl radical in the amide moiety.

WO 99/09013 and WO 00/14071 describe specific 1,3-dimethyl-5-fluoropyrazole-carboxamides and their fungicidal action.

JP-A 09/132,567 discloses pyrazolecarboxamides having a specific mono- or disubstitution in the biphenyl group and a trifluoromethyl group at the pyrazolyl group.

It was an object of the present invention to provide pyrazolecarboxamides whose fungicidal action is improved in comparison with that of the compounds of the prior art.

We have found that this object is achieved by the compounds I defined at the outset.

Moreover, we have found processes for preparing these compounds, compositions comprising them and methods for their use for controlling harmful fungi.

The compounds of the formula I may be present in various crystal modifications whose biological activity may differ. These crystal modifications also form part of the subject matter of the present invention.

The compounds I are generally obtained by reacting a carbonyl halide of the formula II in a manner known per se (for example J. March, Advanced Organic Chemistry, 2nd Ed., 382 f, McGraw-Hill, 1977) in the presence of a base with an aniline of the formula III.

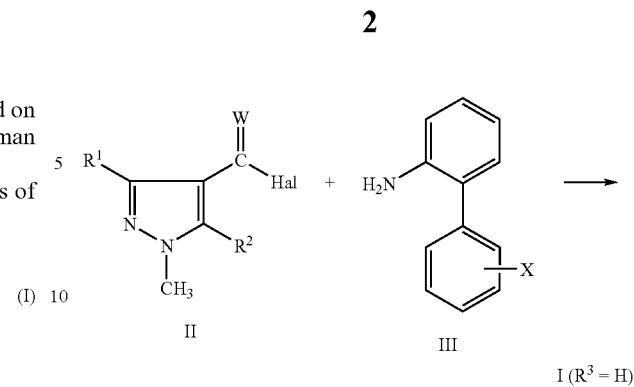

I ($R^3$ = H)

In the formula II, the radical Hal denotes a halogen atom, such as fluorine, chlorine, bromine and iodine, in particular fluorine or chlorine. This reaction is usually carried out at temperatures of from (−20)° C. to 100° C., preferably from 0° C. to 50° C.

Suitable solvents are aliphatic hydrocarbons, such as pentane, hexane, cyclohexane and petroleum ether, aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, ketones, such as acetone, methyl ethyl ketone, diethyl ketone and tert-butyl methyl ketone, alcohols, such as methanol, ethanol, n-propanol, isopropanol, n-butanol and tert-butanol, and also methylene chloride, dimethyl sulfoxide and dimethylformamide, particularly preferably toluene, methylene chloride and tetrahydrofuran.

It is also possible to use mixtures of the solvents mentioned.

Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal oxides, such as lithium oxide, sodium oxide, calcium oxide and magnesium oxide, alkali metal and alkaline earth metal hydrides, such as lithium hydride, sodium hydride, potassium hydride and calcium hydride, alkali metal amides, such as lithium amide, sodium amide and potassium amide, alkali metal and alkaline earth metal carbonates, such as lithium carbonate and calcium carbonate, and also alkali metal bicarbonates, such as sodium bicarbonate, and organometallic compounds, in particular alkali metal alkyls, such as methyllithium, butyllithium and phenyllithium, alkylmagnesium halides, such as methylmagnesium chloride, and also alkali metal and alkaline earth metal alkoxides, such as sodium methoxide, sodium ethoxide, potassium ethoxide, potassium tert-butoxide and dimethoxymagnesium, moreover organic bases, for example tertiary amines, such as trimethylamine, triethylamine, diisopropylethylamine and N-methylpiperidine, pyridine, substituted pyridines, such as collidine, lutidine and 4-dimethylaminopyridine, and also bicyclic amines.

Particular preference is given to using triethylamine and pyridine.

The bases are generally employed in approximately equimolar amounts, based on the compound II. However, they can also be used in an excess of from 5 mol % to 30 mol %, preferably from 5 mol % to 10 mol %, or—if tertiary amines are used—, if appropriate, as solvents.

The starting materials are generally reacted with one another in equimolar amounts. In terms of yield, it may be advantageous to employ II in an excess of from 1 mol % to 20 mol %, preferably from 1 mol % to 10 mol %, based on III.

The starting materials of the formulae II and III required for preparing the compounds I are known or can be synthesized analogously to the known compounds (Helv. Chim. Acta, 60, 978 (1977); Zh. Org. Khim., 26, 1527 (1990); Heterocycles 26, 1885 (1987); Izv. Akad. Nauk. SSSR Ser. Khim., 2160 (1982); THL 28, 593 (1987); THL 29, 5463 (1988)).

Furthermore, it has been found that compounds of the formula I are obtained by reacting, in a known manner, carboxylic acids of the formula IV with an aniline of the formula III in the presence of dehydrating agents and, if desired, an organic base.

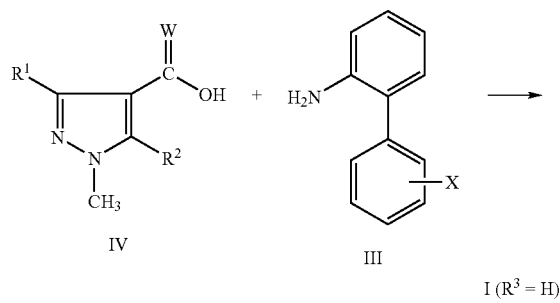

Suitable solvents are aliphatic hydrocarbons, such as pentane, hexane, cyclohexane and petroleum ether, aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, ketones, such as acetone, methyl ethyl ketone, diethyl ketone and tert-butyl methyl ketone, and also dimethyl sulfoxide and dimethylformamide, particularly preferably methylene chloride, toluene and tetrahydrofuran.

It is also possible to use mixtures of the solvents mentioned.

Suitable dehydrating agents are for example 1,1'-carbonyldiimidazole, bis(2-oxo-3-oxazolidinyl)phosphoryl chloride, carbodiimides, such as N,N'-dicyclohexylcarbodiimide, N-(3-dimethylaminopropyl)-N'-ethylcarbodiimide, phosphonium salts, such as (benzotriazol-1-yloxy)tris(dimethylamino)phosphonium hexafluorophosphate, bromotripyrrolidinophosphonium hexafluorophosphate, bromotris(dimethylamino)phosphonium hexafluorophosphate, chlorotripyrrolidinophosphonium hexafluorophosphate, uronium and thiuronium salts, such as O-(benzotriazol-1-yl)-N,N,N',N'-tetramethyluronium hexafluorophosphate, O-(7-azabenzotriazol-1-yl)-N,N,N',N'-tetramethyluronium hexafluorophosphate, S-(1-oxido-2-pyridyl)-N,N,N',N'-tetramethylthiuronium tetrafluoroborate, O-(2-oxo-1(2H)pyridyl)-N,N,N',N'-tetramethyluronium tetrafluoroborate, O-[(ethoxycarbonyl)cyanomethylenamino]-N,N,N',N'-tetramethyluronium tetrafluoroborate, carbenium salts, such as (benzotriazol-1-yloxy)dipyrrolidinocarbenium hexafluorophosphate, (benzotriazol-1-yloxy)dipiperidinocarbenium hexafluorophosphate, O-(3,4-dihydro-4-oxo-1,2,3-benzotriazin-3-yl)-N,N,N',N'-tetramethyluronium tetrafluoroborate, chloro-N',N'-bis(tetramethylene)-formamidinium tetrafluoroborate, chlorodipyrrolidinocarbenium hexafluorophosphate, chloro-N,N,N',N'-bis(pentamethylene)formamidinium tetrafluoroborate, imidazolium salts, such as 2-chloro-1,3-dimethylimidazolidinium tetrafluoroborate, preferably 1,1'-carbonyldiimidazole, bis(2-oxo-3-oxazolidinyl)phosphoryl chloride, N,N'-dicyclohexylcarbodiimide and N-(3-dimethylaminopropyl)-N'-ethylcarbodiimide.

Suitable organic bases are for example tertiary amines, such as trimethylamine, triethylamine, diisopropylethylamine and N-methylpiperidine, pyridine, substituted pyridines, such as collidine, lutidine and 4-dimethylaminopyridine, and also bicyclic amines. Particular preference is given to using triethylamine and pyridine. The bases are generally employed in an excess of from 10 mol % to 200 mol %, preferably from 50 mol % to 150 mol %, based on the compound IV.

The starting materials are generally reacted with one another in approximately equimolar amounts. In terms of yield, it may be advantageous to use an excess of from 1 mol % to 20 mol %, preferably from 1 mol % to 10 mol %, of one of the compounds. The dehydrating agents are generally employed in an excess of from 5 mol % to 100 mol %, preferably from 5 mol % to 60 mol %.

The starting materials of the formulae III and IV required for preparing the compounds I are known or can be synthesized analogously to the known compounds.

The compounds of the formula I where $R^3 \neq$ hydrogen are preferably obtained by reacting compounds of the formula I where $R^3=$H in a known manner in the presence of a base with an alkylating agent:

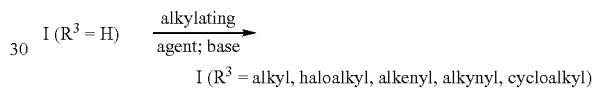

Suitable solvents are aliphatic hydrocarbons, such as pentane, hexane, cyclohexane and petroleum ether, aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane, anisole and tetrahydrofuran, and also dimethyl sulfoxide and dimethylformamide, particularly preferably diethyl ether, tert-butyl methyl ether, tetrahydrofuran and dimethylformamide.

It is also possible to use mixtures of the solvents mentioned.

Suitable alkylating agents are for example alkyl halides, such as methyl iodide, ethyl iodide, methyl bromide, ethyl bromide, methyl chloride and ethyl chloride, alkyl perfluoroalkylsulfonates, such as methyl trifluoromethylsulfonate and ethyl trifluoromethylsulfonate, alkyl alkylsulfonates, such as methyl methylsulfonate and ethyl methylsulfonate, alkyl arylsulfonates, such as methyl p-tolylsulfonate and ethyl p-tolylsulfonate, oxonium salts, such as trimethyloxonium tetrafluoroborate and triethyloxonium tetrafluoroborate.

Particular preference is given to methyl iodide, ethyl iodide, methyl bromide, ethyl bromide, methyl chloride and ethyl chloride.

Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal oxides, such as lithium oxide, sodium oxide, calcium oxide and magnesium oxide, alkali metal and alkaline earth metal hydrides, such as lithium hydride, sodium hydride, potassium hydride and calcium hydride, alkali metal amides, such as lithium amide, sodium amide and potassium amide, alkali metal and alkaline earth metal carbonates, such as lithium carbonate, sodium carbonate, potassium carbonate and calcium carbonate, and also alkali metal bicarbonates, such as sodium bicarbonate, and organometallic compounds, in particular alkali metal alkyls, such as methyllithium, butyllithium and phenyllithium, alkylmagnesium halides, such as methylmagnesium chloride, and also alkali metal and alkaline earth metal alkoxides, such as sodium methoxide, sodium ethoxide, potassium ethoxide and potassium tert-butoxide.

Particular preference is given to using sodium carbonate, potassium carbonate, sodium hydride, potassium hydride, butyllithium and potassium tert-butoxide.

The bases are generally employed in approximately equimolar amounts, based on the compound I. However, they can also be used in an excess of from 5 mol % to 30 mol %, preferably from 5 mol % to 10 mol %.

The starting materials are generally reacted with one another in approximately equimolar amounts. In terms of yield, it may be advantageous to employ the alkylating agent in an excess of from 1 mol % to 20 mol %, preferably from 1 mol % to 10 mol %, based on I.

Those pyrazolecarboxamides I in which W is sulfur can be prepared, for example, by sulfurization of the corresponding compounds I where X acts as oxygen (cf. for example, D. Petrova & K. Jakobcic, Croat. Chem. Acta 48, 49 (1976) and also WO 01/42223).

With a view to their use in fungicidal compositions, suitable compounds of the formula I are those in which the substituents are as defined below:

Halogen is fluorine, chlorine, bromine or iodine;

$C_1$-$C_4$-alkyl is methyl, ethyl, n-propyl, 1-methylethyl, n-butyl, 1-methylpropyl, 2-methylpropyl or 1,1-dimethylethyl;

$C_1$-$C_4$-haloalkyl is a partially or fully halogenated $C_1$-$C_4$-alkyl radical, where the halogen atom(s) is/are in particular fluorine, chlorine and/or bromine, i.e., for example, chloromethyl, bromomethyl, dichloromethyl, trichloromethyl, fluoromethyl, difluoromethyl, trifluoromethyl, chlorofluoromethyl, dichlorofluoromethyl, dhlorodifluoromethyl, 1-chloroethyl, 1-bromoethyl, 1-fluoroethyl, 2-fluoroethyl, 2,2-difluoroethyl, 2-chloro-2-fluoroethyl, 2,2,2-trifluoroethyl, 2-chloro-1,1,2-trifluoroethyl, 2-chloro-2,2-difluoroethyl, 2-bromo-2,2-difluoroethyl, 2,2-dichloro-2-fluoroethyl, 2,2,2-trichloroethyl, 1,1,2,2-tetrafluoroethyl, 1,1,2,2-tetrachloroethyl, pentafluoroethyl, 2,2,3,3-tetrafluoro-1-propyl, 1,1,2,3,3,3-hexafluoro-1-propyl, 1,1,1,3,3,3-hexafluoro-2-propyl, heptafluoro-1-propyl, heptafluoro-2-propyl, 2,2,3,3,4,4,4-heptafluoro-1-butyl or nonafluoro-1-butyl, in particular halomethyl, particularly preferably $CH_2$—Cl, $CH(Cl)_2$, $CH_2$—F, $CH(F)_2$, $CF_3$, CHFCl, $CF_2Cl$ or $CF(Cl)_2$;

$C_2$-$C_4$-alkenyl is a straight-chain or branched hydrocarbon radical having 2, 3 or 4 carbon atoms and one or two double bonds, for example vinyl, allyl, 2-propenyl, 1-butenyl, 2-butenyl, 3-butenyl, 1-methyl-1-propenyl, 2-methyl-1-propenyl, 1-methyl-2-propenyl or 2-methyl-2-propenyl, in particular allyl;

$C_2$-$C_4$-alkynyl is a straight-chain or branched hydrocarbon radical having 2, 3 or 4 carbon atoms and one triple bond, for example ethynyl, 1-propynyl, 2-propynyl, 1-butynyl, 2-butynyl, 3-butynyl or 1-methyl-2-propynyl, in particular ethynyl, 1-propynyl or 2-propynyl;

$C_3$-$C_6$-cycloalkyl is cyclopropyl, cyclobutyl, cyclopentyl or cyclohexyl.

With a view to the biological activity of the compounds I, the following meanings of the variables are preferred, in each case on their own or in combination:

$R^1$ fluorine, chlorine, methyl, fluoromethyl, difluoromethyl, chlorofluoromethyl, chlorodifluoromethyl, dichlorofluoromethyl or trifluoromethyl, particularly preferably methyl, fluoromethyl, difluoromethyl, chlorofluoromethyl or trifluoromethyl, in particular difluoromethyl or trifluoromethyl, very particularly preferably difluoromethyl;

$R^2$ hydrogen, fluorine, chlorine or methyl, particularly preferably hydrogen, fluorine or chlorine, in particular hydrogen or chlorine, very particularly preferably hydrogen;

$R^3$ hydrogen, methyl or ethyl, particularly preferably hydrogen or methyl, in particular hydrogen;

W oxygen.

Particular preference is given to compounds I having the following substituent combinations in which the variables are as defined below:

$R^1$ fluorine, chlorine, methyl, fluoromethyl, difluoromethyl, chlorofluoromethyl, chlorodifluoromethyl, dichlorofluoromethyl or trifluoromethyl, in particular fluorine, chlorine, fluoromethyl, difluoromethyl, chlorofluoromethyl, chlorodifluoromethyl, dichlorofluoromethyl or trifluoromethyl, very particularly preferably fluorine, chlorine, fluoromethyl, difluoromethyl, chlorofluoromethyl, chlorodifluoromethyl or dichlorofluoromethyl;

$R^2$ hydrogen, fluorine, chlorine or methyl, in particular hydrogen, fluorine or chlorine, very particularly preferably hydrogen or chlorine;

$R^3$ hydrogen, methyl or ethyl, in particular hydrogen or methyl, very particularly preferably hydrogen;

W oxygen.

Preference is furthermore also given to combinations of substituents having the following meanings:

$R^1$ fluorine, chlorine, methyl, fluoromethyl, difluoromethyl, chlorofluoromethyl, or chlorodifluoromethyl;

$R^2$ hydrogen, fluorine, chlorine or methyl, in particular hydrogen, fluorine or chlorine, very particularly preferably hydrogen or chlorine;

$R^3$ hydrogen, methyl or ethyl, particularly preferably hydrogen or methyl, in particular hydrogen;

W oxygen.

Preference is furthermore also given to combinations of substituents having the following meanings:

$R^1$ fluoromethyl, difluoromethyl, chlorofluoromethyl or dichlorofluoromethyl, in particular difluoromethyl, chlorofluoromethyl or dichlorofluoromethyl, very particularly preferably difluoromethyl;

$R^2$ hydrogen, fluorine, chlorine or methyl, in particular hydrogen, fluorine or chlorine, very particularly preferably hydrogen;

$R^3$ hydrogen, methyl or ethyl, in particular hydrogen;

W oxygen.

Particular preference is also given to compounds I in which $R^1$ is methyl, $R^2$ is hydrogen, chlorine or methyl, in particular hydrogen or chlorine, $R^3$ is hydrogen, methyl or ethyl, in particular hydrogen, and W is oxygen.

Particular preference is also given to compounds I in which $R^1$ is trifluoromethyl, $R^2$ is chlorine or methyl, in particular chlorine, $R^3$ is hydrogen, methyl or ethyl, in particular hydrogen, and W is oxygen.

One embodiment of the invention comprises providing pyrazolecarboxamides I where X is in the ortho-position (=compounds Ia):

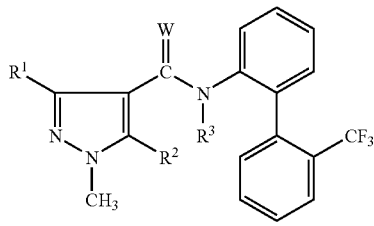

(Ia)

A further embodiment of the invention comprises providing pyrazolecarboxamides I where X is in the meta-position (=compounds Ib):

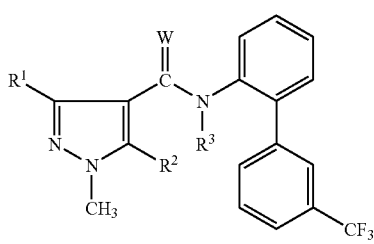

(Ib)

A further embodiment of the invention comprises providing pyrazolecarboxamides I where X is in the para-position (=compounds Ic):

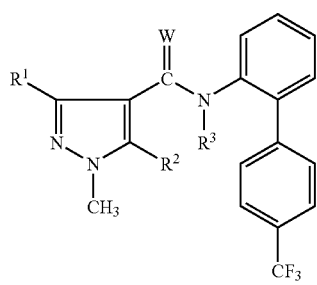

(Ic)

In particular with a view to their use as fungicides, preference is given to the compounds of the formula I-A.

TABLE A

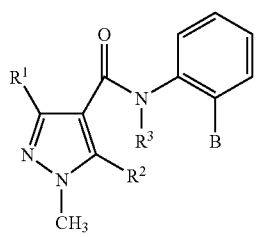

(I-A)

| No. | B | $R^1$ |
|---|---|---|
| 1 | 2-trifluoromethylphenyl | $CF_3$ |
| 2 | 3-trifluoromethylphenyl | $CF_3$ |
| 3 | 4-trifluoromethylphenyl | $CF_3$ |
| 4 | 2-trifluoromethylphenyl | $CHF_2$ |

TABLE A-continued (I-A)

| No. | B | $R^1$ |
|---|---|---|
| 5 | 3-trifluoromethylphenyl | $CHF_2$ |
| 6 | 4-trifluoromethylphenyl | $CHF_2$ |
| 7 | 2-trifluoromethylphenyl | $CH_2F$ |
| 8 | 3-trifluoromethylphenyl | $CH_2F$ |
| 9 | 4-trifluoromethylphenyl | $CH_2F$ |
| 10 | 2-trifluoromethylphenyl | $CHFCl$ |
| 11 | 3-trifluoromethylphenyl | $CHFCl$ |
| 12 | 4-trifluoromethylphenyl | $CHFCl$ |
| 13 | 2-trifluoromethylphenyl | $CF_2Cl$ |
| 14 | 3-trifluoromethylphenyl | $CF_2Cl$ |
| 15 | 4-trifluoromethylphenyl | $CF_2Cl$ |
| 16 | 2-trifluoromethylphenyl | $CFCl_2$ |
| 17 | 3-trifluoromethylphenyl | $CFCl_2$ |
| 18 | 4-trifluoromethylphenyl | $CFCl_2$ |
| 19 | 2-trifluoromethylphenyl | $CH_3$ |
| 20 | 3-trifluoromethylphenyl | $CH_3$ |
| 21 | 4-trifluoromethylphenyl | $CH_3$ |

Table 1:
Compounds of the formula I-A in which $R^2$ and $R^3$ are hydrogen and $R^1$ and B for each individual compound correspond in each case to one row of Table A, except for rows 1-3.

Table 2:
Compounds of the formula I-A in which $R^2$ is chlorine and $R^3$ is hydrogen and $R^1$ and B for each individual compound correspond in each case to one row of Table A.

Table 3:
Compounds of the formula I-A in which $R^2$ is fluorine and $R^3$ is hydrogen and $R^1$ and B for each individual compound correspond in each case to one row of Table A, except for rows 1 to 3 and 19 to 21.

Table 4:
Compounds of the formula I-A in which $R^2$ is hydrogen and $R^3$ is methyl and $R^1$ and B for each individual compound correspond in each case to one row of Table A.

Table 5:
Compounds of the formula I-A in which $R^2$ is hydrogen and $R^3$ is ethyl and $R^1$ and B for each individual compound correspond in each case to one row of Table A.

Very particular preference is given to the following pyrazolecarboxamides of the formula I:
N-(4'-trifluoromethylbiphenyl-2-yl)-3-difluoromethyl-1-methyl-1H-pyrazole-4-carboxamide, N-(3'-trifluoromethylbiphenyl-2-yl)-3-difluoromethyl-1-methyl-1H-pyrazole-4-carboxamide, N-(2'-trifluoromethylbiphenyl-2-yl)-3-difluoromethyl-1-methyl-1H-pyrazole-4-carboxamide, N-(4'-trifluoromethylbiphenyl-2-yl)-5-chloro-1,3-dimethyl-1H-pyrazole-4-carboxamide, N-(4'-trifluoromethylbiphenyl-2-yl)-1,3-dimethyl-1H-pyrazole-4-carboxamide, N-(4'-trifluoromethylbiphenyl-2-yl)-3-fluoromethyl-1-methyl-1H-pyrazole-4-carboxamide, N-(4'-trifluoromethylbiphenyl-2-yl)-3-chlorodifluoromethyl-1- methyl-1H-pyrazole-4-carboxamide and N-(4'-trifluoromethylbiphenyl-2-yl)-3-chlorofluoromethyl-1-methyl-1H-pyrazole-4-carboxamide.

The compounds I are suitable as fungicides. They are distinguished by an outstanding effectiveness against a broad spectrum of phytopathogenic fungi, especially from the classes of the Ascomycetes, Deuteromycetes, Oomycetes and Basidiomycetes. Some are systemically effective and they can be used in plant protection as foliar fungicides, as fungicides for seed dressing and as soil fungicides.

They are particularly important in the control of a multitude of fungi on various cultivated plants, such as wheat, rye, barley, oats, rice, corn, grass, bananas, cotton, soya, coffee, sugar cane, vines, fruits and ornamental plants, and vegetables, such as cucumbers, beans, tomatoes, potatoes and cucurbits, and on the seeds of these plants.

They are especially suitable for controlling the following plant diseases:

*Alternaria* species on vegetables, oilseed rape, sugar beet and fruit and rice, such as, for example, *A. solani* or *A. alternata* on potatoes and tomatoes;
*Aphanomyces* species on sugar beet and vegetables;
*Ascochyta* species on cereals and vegetables;
*Bipolaris* and *Drechslera* species on corn, cereals, rice and lawns, such as, for example, *D. maydis* on corn;
*Blumeria graminis* (powdery mildew) on cereals;
*Botrytis cinerea* (gray mold) on strawberries, vegetables, flowers and grapevines;
*Bremia lactucae* on lettuce;
*Cercospora* species on corn, soybeans, rice and sugar beet;
*Cochliobolus* species on corn, cereals, rice, such as, for example *Cochliobolus sativus* on cereals, *Cochliobolus miyabeanus* on rice;
*Colletotricum* species on soybeans and cotton;
*Drechslera* species, *Pyrenophora* species on corn, cereals, rice and lawns, such as, for example, *D. teres* on barley or *D. tritici-repentis* on wheat;
*Esca* on grapevines, caused by *Phaeoacremonium chlamydosporium*, *Ph. Aleophilum* and *Formitipora punctata* (syn. *Phellinus punctatus*);
*Exserohilum* species on corn;
*Erysiphe cichoracearum* and *Sphaerotheca fuliginea* on cucumbers;
*Fusarium* and *Verticillium* species on various plants, such as, for example, *F. graminearum* or *F. culmorum* on cereals or *F. oxysporum* on a multitude of plants, such as, for example, tomatoes;
*Gaeumanomyces graminis* on cereals;
*Gibberella* species on cereals and rice (for example *Gibberella fujikuroi* on rice);
Grainstaining complex on rice;
*Helminthosporium* species on corn and rice;
*Michrodochium nivale* on cereals;
*Mycosphaerella* species on cereals, bananas and groundnuts, such as, for example, *M. graminicola* on wheat or *M. fijiensis* on bananas;
*Peronospora* species on cabbage and bulbous plants, such as, for example, *P. brassicae* on cabbage or *P. destructor* on onions;
*Phakopsara pachyrhizi* and *Phakopsara meibomiae* on soybeans;
*Phomopsis* species on soybeans and sunflowers;
*Phytophthora infestans* on potatoes and tomatoes;
*Phytophthora* species on various plants, such as, for example, *P. capsici* on bell pepper;
*Plasmopara viticola* on grapevines;
*Podosphaera leucotricha* on apples;
*Pseudocercosporella herpotrichoides* on cereals;
*Pseudoperonospora* on various plants, such as, for example, *P. cubensis* on cucumber or *P. humili* on hops;
*Puccinia* species on various plants, such as, for example, *P. triticina*, *P. striformins*, *P. hordei* or *P. graminis* on cereals or *P. asparagi* on asparagus;
*Pyricularia oryzae*, *Corticium sasakii*, *Sarocladium oryzae*, *S. attenuatum*, *Entyloma oryzae* on rice;
*Pyricularia grisea* on lawns and cereals;
*Pythium* spp. on lawns, rice, corn, cotton, oilseed rape, sunflowers, sugar beet, vegetables and other plants, such as, for example, *P. ultiumum* on various plants, *P. aphanidermatum* on lawns;
*Rhizoctonia* species on cotton, rice, potatoes, lawns, corn, oilseed rape, potatoes, sugar beet, vegetables and on various plants, such as, for example, *R. solani* on beet and various plants;
*Rhynchosporium secalis* on barley, rye and triticale;
*Sclerotinia* species on oilseed rape and sunflowers;
*Septoria tritici* and *Stagonospora nodorum* on wheat;
*Erysiphe* (syn. *Uncinula*) *necator* on grapevines;
*Setospaeria* species on corn and lawns;
*Sphacelotheca reilinia* on corn;
*Thievaliopsis* species on soybeans and cotton;
*Tilletia* species on cereals;
*Ustilago* species on cereals, corn and sugar cane, such as, for example, *U. maydis* on corn;
*Venturia* species (scab) on apples and pears, such as, for example, *V. inaequalis* on apples.

They are particularly suitable for controlling harmful fungi from the class of the *Peronosporomycetes* (syn. *Oomycetes*) such as *Peronospora* species, *Phytophthera* species, *Plasmopara viticola*, *Pseudoperonospora* species and *Pythium* species.

The compounds I are also suitable for controlling harmful fungi in the protection of materials (for example wood, paper, paint dispersions, fibers or fabrics) and in the protection of stored products. In the protection of wood, particular attention is paid to the following harmful fungi:

Ascomycetes, such as *Ophiostoma* spp., *Ceratocystis* spp., *Aureobasidium pullulans*, *Sclerophoma* spp., *Chaetomium* spp., *Humicola* spp., *Petriella* spp., *Trichurus* spp.; Basidiomycetes, such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes, such as *Aspergillus* spp., *Cladosporium* spp., *Penicillium* spp., *Trichoderma* spp., *Alternaria* spp., *Paecilomyces* spp. and Zygomycetes, such as *Mucor* spp., additionally in the protection of materials the following yeasts: *Candida* spp. and *Saccharomyces cerevisae*.

The compounds I are employed by treating the fungi or the plants, seeds, materials or soil to be protected from fungal attack with a fungicidally effective amount of the active compounds. The application can be carried out both before and after the infection of the materials, plants or seeds by the fungi.

The fungicidal compositions generally comprise from 0.1 to 95%, preferably from 0.5 to 90%, by weight of active compound.

When employed in plant protection, the amounts applied are, depending on the kind of effect desired, from 0.01 to 2.0 kg of active compound per hectare.

In seed treatment, amounts of active compound of from 1 g to 1000 g per 100 kg, preferably from 5 g to 100 g per 100 kg, of seed are generally required.

When used in the protection of materials or stored products, the amount of active compound applied depends on the kind of application area and on the desired effect. Amounts customarily applied in the protection of materials are, for example, 0.001 g to 2 kg, preferably 0.005 g to 1 kg, of active compound per cubic meter of treated material.

The compounds I can be converted into the customary formulations, for example solutions, emulsions, suspensions, dusts, powders, pastes and granules. The application form depends on the particular purpose; in each case, it should ensure a fine and uniform distribution of the compound according to the invention.

The formulations are prepared in a known manner, for example by extending the active compound with solvents and/or carriers, if desired using emulsifiers and dispersants. Solvents/auxiliaries which are suitable for this purpose are essentially:

water, aromatic solvents (for example Solvesso® products, xylene), paraffins (for example mineral oil fractions), alcohols (for example methanol, butanol, pentanol, benzyl alcohol), ketones (for example cyclohexanone, gammabutyrolactone), pyrrolidones (N-methylpyrrolidone, N-octylpyrrolidone), acetates (glycol diacetate), glycols, fatty acid dimethylamides, fatty acids and fatty acid esters. In principle, solvent mixtures may also be used.

carriers such as ground natural minerals (for example kaolins, clays, talc, chalk) and ground synthetic minerals (for example highly disperse silica, silicates); emulsifiers such as nonionic and anionic emulsifiers (for example polyoxyethylene fatty alcohol ethers, alkylsulfonates and arylsulfonates) and dispersants such as lignosulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenol polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, strongly polar solvents, for example dimethyl sulfoxide, N-methylpyrrolidone and water.

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of at least one active compound I. The active compounds are employed in a purity of from 90% to 100%, preferably 95% to 100% (according to NMR spectrum).

The following are examples of formulations: 1. Products for dilution with water

A Water-Soluble Concentrates (SL, LS)

10 parts by weight of a compound I according to the invention are dissolved in 90 parts by weight of water or in a water-soluble solvent. As an alternative, wetting agents or other auxiliaries are added. The active compound dissolves upon dilution with water. In this way, a formulation having a content of 10% by weight of active compound is obtained.

B Dispersible Concentrates (DC)

20 parts by weight of a compound I according to the invention are dissolved in 70 parts by weight of cyclohexanone with addition of 10 parts by weight of a dispersant, for example polyvinylpyrrolidone. Dilution with water gives a dispersion. The active compound content is 20% by weight C Emulsifiable Concentrates (EC)

15 parts by weight of a compound I according to the invention are dissolved in 75 parts by weight of xylene with addition of calcium dodecylbenzenesulfonate and castor oil ethoxylate (in each case 5 parts by weight). Dilution with water gives an emulsion. The formulation has an active compound content of 15% by weight.

D Emulsions (EW, EO, ES)

25 parts by weight of a compound I according to the invention are dissolved in 35 parts by weight of xylene with addition of calcium dodecylbenzenesulfonate and castor oil ethoxylate (in each case 5 parts by weight). This mixture is introduced into 30 parts by weight of water by means of an emulsifying machine (Ultraturrax) and made into a homogeneous emulsion. Dilution with water gives an emulsion. The formulation has an active compound content of 25% by weight.

E Suspensions (SC, OD, FS)

In an agitated ball mill, 20 parts by weight of a compound I according to the invention are comminuted with addition of 10 parts by weight of dispersants and wetting agents and 70 parts by weight of water or an organic solvent to give a fine active compound suspension. Dilution with water gives a stable suspension of the active compound. The active compound content in the formulation is 20% by weight.

F Water-Dispersible Granules and Water-Soluble Granules (WG, SG)

50 parts by weight of a compound I according to the invention are ground finely with addition of 50 parts by weight of dispersants and wetting agents and prepared as water-dispersible or water-soluble granules by means of technical appliances (for example extrusion, spray tower, fluidized bed). Dilution with water gives a stable dispersion or solution of the active compound. The formulation has an active compound content of 50% by weight.

G Water-Dispersible Powders and Water-Soluble Powders (WP, SP, SS, WS)

75 parts by weight of a compound I according to the invention are ground in a rotor-stator mill with addition of 25 parts by weight of dispersants, wetting agents and silica gel. Dilution with water gives a stable dispersion or solution of the active compound. The active compound content of the formulation is 75% by weight.

H Gel Formulations (GF)

In a ball mill, 20 parts by weight of a compound I according to the invention, 10 parts by weight of dispersant, 1 part by weight of gelling agent and 70 parts by weight of water or an organic solvent are ground to give a fine suspension. On dilution with water, a stable suspension having an active compound content of 20% by weight is obtained.

2. Products to be Applied Undiluted

J Dustable Powders (DP, DS)

5 parts by weight of a compound I according to the invention are ground finely and mixed intimately with 95 parts by weight of finely divided kaolin. This gives a dustable product having an active compound content of 5% by weight.

K Granules (GR, FG, GG, MG)

0.5 part by weight of a compound I according to the invention is ground finely and associated with 99.5 parts by weight of carriers. Current methods are extrusion, spray-drying and the fluidized bed. This gives granules to be applied undiluted having an active compound content of 0.5% by weight.

L ULV solutions (UL)

10 parts by weight of a compound I according to the invention are dissolved in 90 parts by weight of an organic solvent, for example xylene. This gives a product to be applied undiluted having an active compound content of 10% by weight.

For seed treatment, use is usually made of water-soluble concentrates (LS), suspensions (FS), dustable powders (DS), water-dispersible and water-soluble powders (WS, SS), emulsions (ES), emulsifiable concentrates (EC) and gel formulations (GF). These formulations can be applied to the seed in undiluted form or, preferably, diluted. Application can be carried out prior to sowing.

The active compounds can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; the intention is to ensure in each case the finest possible distribution of the active compounds I according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10%, preferably from 0.01 to 1%.

The active compounds may also be used successfully in the ultra-low-volume (ULV) process, by which it is possible to apply formulations comprising over 95% by weight of active compound, or even to apply the active compound without additives.

Various types of oils, wetters, adjuvants, herbicides, fungicides, other pesticides, or bactericides may be added to the active compounds, if appropriate not until immediately prior to use (tank mix). These agents are usually admixed with the agents according to the invention in a weight ratio of 1:100 to 100:1, preferably 1:10 to 10:1.

Suitable adjuvants in this sense are in particular: organically modified polysiloxanes, for example Break Thru S 240®; alcohol alkoxylates, for example Atplus 245®, Atplus MBA 1303®, Plurafac LF 300® and Lutensol® ON 30; EO/PO block polymers, for example Pluronic® RPE 2035 and Genapol® B; alcohol ethoxylates, for example Lutensol® XP 80; and sodium dioctylsulfosuccinate, for example Leophen® RA.

The compositions according to the invention can, in the use form as fungicides, also be present together with other active compounds, e.g. with herbicides, insecticides, growth regulators such as prohexadione Ca, fungicides or else with fertilizers. Mixing the compounds I or the compositions comprising them with one or more further active compounds, in particular fungicides, it is in many cases possible to broaden the activity spectrum or to prevent the development of resistance. In many cases, synergistic effects are obtained.

The following list of fungicides, in conjunction with which the compounds according to the invention can be used, is intended to illustrate the possible combinations but does not limit them:

strobilurins azoxystrobin, dimoxystrobin, enestroburin, fluoxastrobin, kresoxim-methyl, metominostrobin, picoxystrobin, pyraclostrobin, trifloxystrobin, orysastrobin, methyl (2-chloro-5-[1-(3-methylbenzyloxyimino)ethyl]benzyl)carbamate, methyl (2-chloro-5-[1-(6-methylpyridin-2-ylmethoxyimino)ethyl]benzyl)carbamate, methyl 2-(ortho(2,5-dimethylphenyloxymethylene)phenyl)-3-methoxyacrylate;

carboxamides
  carboxanilides: benalaxyl, benodanil, boscalid, carboxin, mepronil, fenfuram, fenhexamid, flutolanil, furametpyr, metalaxyl, ofurace, oxadixyl, oxycarboxin, penthiopyrad, thifluzamide, tiadinil, N-(4'-bromobiphenyl-2-yl)-4-difluoromethyl-2-methylthiazole-5-carboxamide, N-(4'-trifluoromethylbiphenyl-2-yl)-4-difluoromethyl-2-methylthiazole-5-carboxamide, N-(4'-chloro-3'-fluorobiphenyl-2-yl)-4-difluoromethyl-2-methylthiazole-5-carboxamide, N-(3',4'-dichloro-4-fluorobiphenyl-2-yl)-3-difluoromethyl-1-methylpyrazole-4-carboxamide, N-(2-cyanophenyl)-3,4-dichloroisothiazole-5-carboxamide;
  carboxylic acid morpholides: dimethomorph, flumorph;
  benzamides: flumetover, fluopicolide (picobenzamid), zoxamide;
  other carboxamides: carpropamid, diclocymet, mandipropamid, N-(2-(4-[3-(4-chlorophenyl)prop-2-ynyloxy]-3-methoxyphenyl)ethyl)-2-methanesulfonylamino-3-methylbutyramide, N-(2-(4-[3-(4-chlorophenyl)prop-2-ynyloxy]-3-methoxyphenyl)ethyl)-2-ethanesulfonylamino-3-methylbutyramide;

azoles
  triazoles: bitertanol, bromuconazole, cyproconazole, difenoconazole, diniconazole, enilconazole, epoxiconazole, fenbuconazole, flusilazole, fluquinconazole, flutriafol, hexaconazole, imibenconazole, ipconazole, metconazole, myclobutanil, penconazole, propiconazole, prothioconazole, simeconazole, tebuconazole, tetraconazole, triadimenol, triadimefon, triticonazole;

imidazoles: cyazofamid, imazalil, pefurazoate, prochloraz, triflumizole;
benzimidazoles: benomyl, carbendazim, fuberidazole, thiabendazole;
others: ethaboxam, etridiazole, hymexazole;

nitrogenous heterocyclyl compounds
pyridines: fluazinam, pyrifenox, 3-[5-(4-chlorophenyl)-2,3-dimethylisoxazolidin-3-yl]-pyridine;
pyrimidines: bupirimate, cyprodinil, ferimzone, fenarimol, mepanipyrim, nuarimol, pyrimethanil;
piperazines: triforine;
pyrroles: fludioxonil, fenpiclonil;
morpholines: aldimorph, dodemorph, fenpropimorph, tridemorph;
dicarboximides: iprodione, procymidone, vinclozolin;
others: acibenzolar-S-methyl, anilazine, captan, captafol, dazomet, diclomezine, fenoxanil, folpet, fenpropidin, famoxadone, fenamidone, octhilinone, probenazole, proquinazid, pyroquilon, quinoxyfen, tricyclazole, 5-chloro-7-(4-methylpiperidin-1-yl)-6-(2,4,6-trifluorophenyl)-[1,2,4]triazolo[1,5-a]pyrimidine, 2-butoxy-6-iodo-3-propylchromen-4-one, N,N-dimethyl-3-(3-bromo-6-fluoro-2-methylindole-1-sulfonyl)-[1,2,4]triazole-1-sulfonamide;

carbamates and dithiocarbamates
dithiocarbamates: ferbam, mancozeb, maneb, metiram, metam, propineb, thiram, zineb, ziram;
carbamates: diethofencarb, flubenthiavalicarb, iprovalicarb, propamocarb, methyl 3-(4-chlorophenyl)-3-(2-isopropoxycarbonylamino-3-methylbutyrylamino)propionate, 4-fluorophenyl N-(1-(1-(4-cyanophenyl)ethanesulfonyl)but-2-yl)carbamate;

other fungicides
guanidines: dodine, iminoctadine, guazatine;
antibiotics: kasugamycin, polyoxins, streptomycin, validamycin A;
organometallic compounds: fentin salts;
sulfur-containing heterocyclyl compounds: isoprothiolane, dithianon;
organophosphorus compounds: edifenphos, fosetyl, fosetyl-aluminum, iprobenfos, pyrazophos, toiclofos-methyl, phosphorous acid and its salts;
organochlorine compounds: thiophanate-methyl, chlorothalonil, dichlofluanid, tolylfluanid, flusulfamide, phthalide, hexachlorobenzene, pencycuron, quintozene;
nitrophenyl derivatives: binapacryl, dinocap, dinobuton;
inorganic active compounds: Bordeaux mixture, copper acetate, copper hydroxide, copper oxychloride, basic copper sulfate, sulfur;
others: spiroxamine, cyflufenamid, cymoxanil, metrafenone.

SYNTHESIS EXAMPLES

Example 1

N-(4'-Trifluoromethylbiphenyl-2-yl)-3-difluoromethyl-1-methyl-1H-pyrazole-4-carboxamide (comp. I.1)

At room temperature, 0.29 g of 3-difluoromethyl-1-methyl-1H-pyrazole-4-carbonyl chloride was added dropwise to a solution of 0.36 g of 4'-trifluoromethyl-2-aminobiphenyl and 0.18 g of pyridine in 10 ml of toluene, after which the mixture was stirred at room temperature for 16 hours. 30 ml of methyl tert-butyl ether were added, and the organic phase was washed successively with 2% strength hydrochloric acid, 2% strength aqueous sodium hydroxide solution and then with dilute sodium chloride solution. The organic phase was dried and concentrated under reduced pressure. The crude product was stirred with 5 ml of diisopropyl ether. The solid that remained was separated off and dried. This gave 0.45 g of the desired product as a white powder; m.p. 164-165° C.

The compounds of the formula I (in which W is O) listed in Table 6 below were prepared by the procedures given above.

TABLE 6

| Active compound | $R^1$ | $R^2$ | $R^3$ | X | Characterization (m.p. or $^1$H-NMR) |
|---|---|---|---|---|---|
| I.1 | $CHF_2$ | H | H | 4-$CF_3$ | 164-165 |
| I.2 | $CHF_2$ | H | H | 3-$CF_3$ | 124-125 |
| I.3 | $CHF_2$ | H | H | 2-$CF_3$ | 133-134 |
| I.4 | $CH_3$ | Cl | H | 4-$CF_3$ | 173-175 |
| I.5 | $CH_3$ | H | H | 4-$CF_3$ | 174-177 |
| I.6 | $CH_2F$ | H | H | 4-$CF_3$ | 156-158 |
| I.7 | $CF_2$—Cl | H | H | 4-$CF_3$ | 193-196 |
| I.8 | CHF—Cl | H | H | 4-$CF_3$ | 181-186 |

Use Examples

The active compounds were prepared as a stock solution comprising 25 mg of active compound I which was made up to 10 ml using a mixture of acetone and/or dimethyl sulfoxide and the emulsifier Uniperol® EL (wetting agent having emulsifying and dispersing action based on ethoxylated alkylphenols) in a volume ratio of solvent/emulsifier of 99 to 1. The mixture was then made up with water to 100 ml. This stock solution was diluted with the solvent/emulsifier/water mixture described to the concentration of active compounds stated below.

Protective Activity Against *Puccinia recondita* on Wheat (Brown Rust of Wheat)

Leaves of potted wheat seedlings of the cultivar "Kanzler" were sprayed to runoff point with an aqueous suspension having the concentration of active compound stated below. The next day the treated plants were inoculated with a spore suspension of brown rust of wheat (*Puccinia recondita*). The plants were then placed in a chamber at high atmospheric humidity (90 to 95%) at 20 to 22° C. for 24 hours. During this time, the spores germinated and the germ tubes penetrated into the leaf tissue. The next day, the test plants were returned to the greenhouse and cultivated at temperatures between 20 and 22° C. and 65 to 70% relative atmospheric humidity for a further 7 days. The extent of the rust fungus development on the leaves was then determined visually.

In this test, the plants which had been treated with 250 ml of compounds I.1, I.2 and I.3 from Table 6 showed an infection of at most 7%, whereas the untreated plants were 90% infected.

Activity Against Net Blotch of Barley Caused by *Pyrenophora teres*, 1 Day Protective Application Leaves of potted barley seedlings were sprayed to runoff point with an aqueous suspension having the concentration of active compound stated below. 24 hours after the spray coating had dried on, the test plants were inoculated with an aqueous spore suspension of *Pyrenophora* [syn. *Drechslera*] *teres*, the net blotch pathogen. The test plants were then placed in a greenhouse at temperatures between 20 and 24° C. and at 95 to 100% relative atmospheric humidity. After 6 days, the extent of the development of the disease was determined visually in % infection of the entire leaf area.

In this test, the plants which had been treated with 250 ml of compounds I.1, I.2 and I.3 from Table 6 showed an infection of at most 7%, whereas the untreated plants were 90% infected.

The invention claimed is:

1. A pyrazolecarboxamide of the formula I

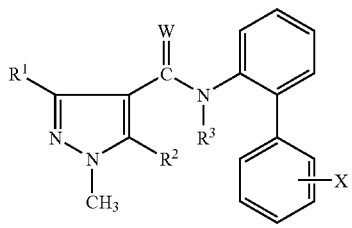

in which the variables are as defined below:
X is trifluoromethyl;
$R^1$ is F, Cl, bromine, $C_1$-$C_4$-alkyl or $C_1$-$C_4$-haloalkyl;
$R^2$ is hydrogen, halogen or $C_1$-$C_4$-alkyl;
$R^3$ is hydrogen, $C_1$-$C_4$-alkyl, $C_1$-$C_4$-haloalkyl, $C_2$-$C_4$-alkenyl, $C_2$-$C_4$-alkynyl or $C_3$-$C_6$-cycloalkyl;
W is oxygen or sulfur,
with the proviso that, if $R^3$ is hydrogen and W is oxygen,
a) $R^1$ and $R^2$ are not simultaneously methyl and fluorine, respectively;
b) $R^1$ and $R^2$ are not simultaneously trifluoromethyl and hydrogen or fluorine, respectively.

2. The pyrazolecarboxamide of the formula I according to claim 1 in which the variables are as defined below:
$R^1$ is F, chlorine, methyl, fluoromethyl, difluoromethyl, chlorofluoromethyl, chlorodifluoromethyl, dichlorofluoromethyl or trifluoromethyl;
$R^2$ is hydrogen, F, Cl or methyl;
$R^3$ is hydrogen or methyl;
W is oxygen.

3. The pyrazolecarboxamide of the formula I according to claim 1 in which the variables are as defined below:
$R^1$ is F, Cl, methyl, fluoromethyl, difluoromethyl, chlorofluoromethyl, chlorodifluoromethyl, dichlorofluoromethyl or trifluoromethyl;
$R^2$ is hydrogen, F or chlorine;
$R^3$ is hydrogen;
W is oxygen.

4. The pyrazolecarboxamide of the formula I according to claim 1 in which the variables are as defined below:
$R^1$ is F, Cl, methyl, fluoromethyl, difluoromethyl, chlorofluoromethyl, chlorodifluoromethyl, dichlorofluoromethyl or trifluoromethyl;
$R^2$ is hydrogen or chlorine;
$R^3$ is hydrogen;
W is oxygen.

5. The pyrazolecarboxamide of the formula I according to claim 1 in which the variables are as defined below:
$R^1$ is fluorine, chlorine, fluoromethyl, difluoromethyl, chlorofluoromethyl, chlorodifluoromethyl or dichlorofluoromethyl;
$R^2$ is hydrogen, fluorine, chlorine or methyl;
$R^3$ is hydrogen, methyl or ethyl;
W is oxygen.

6. The pyrazolecarboxamide of the formula I according to claim 1 in which the variables are as defined below:
$R^1$ is methyl;
$R^2$ is hydrogen, chlorine or methyl;
$R^3$ is hydrogen, methyl or ethyl;
W is oxygen.

7. The pyrazolecarboxamide of the formula I according to claim 1 in which the variables are as defined below:
$R^1$ is trifluoromethyl;
$R^2$ is chlorine or methyl;
$R^3$ is hydrogen, methyl or ethyl;
W is oxygen.

8. The pyrazolecarboxamide of the formula I according to claim 1, selected from the group consisting of N-(4'-trifluoromethylbiphenyl-2-yl)-3-difluoromethyl-1-methyl-1H-pyrazole-4-carboxamide, N-(3'-trifluoromethylbiphenyl-2-yl)-3-difluoromethyl-1-methyl-1H-pyrazole-4-carboxamide, N-(T-trifluoromethylbiphenyl-2-yl)-3-difluoromethyl-1-methyl-1H-pyrazole-4-carboxamide, N-(4'-trifluoromethylbiphenyl-2-yl)-5-chloro-1,3-dimethyl-1H-pyrazole-4-carboxamide, N-(4'-trifluoromethylbiphenyl-2-yl)-1,3-dimethyl-1H-pyrazole-4-carboxamide, N-(4'-trifluoromethylbiphenyl-2-yl)-3-fluoromethyl-1-methyl-1H-pyrazole-4-carboxamide, N-(4'-trifluoromethylbiphenyl-2-yl)-3-chlorodifluoromethyl-1-methyl-1H-pyrazole-4-carboxamide and N-(4'-trifluoromethyl-biphenyl-2-yl)-3-chlorofluoromethyl-1-methyl-1H-pyrazole-4-carboxamide.

9. A composition for controlling harmful fungi, which comprises a fungicidal amount of at least one compound of the formula I according to claim 1 and at least one inert additive.

10. A method for controlling phytopathogenic harmful fungi which comprises treating the harmful fungi, their habitat and/or the materials, plants, the soil or seed to be protected from fungal attack with a fungicidally effective amount of at least one compound of the formula I according to claim 1.

11. Seed comprising at least one compound of the formula I according to claim 1 in an amount of from 1 to 1000 g per 100 kg of seed.

* * * * *